United States Patent [19]

Cragoe, Jr. et al.

[11] 4,163,781

[45] Aug. 7, 1979

[54] 3-AMINO-N-[(PHOSPHONOAMINO)IMINOMETHYL]-6-HALOPYRAZINECARBOXAMIDE COMPOUNDS, COMPOSITIONS AND METHODS OF USE

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 896,876

[22] Filed: Apr. 17, 1978

[51] Int. Cl.$^2$ .................. A61K 31/675; C07D 241/32
[52] U.S. Cl. .................................. 424/200; 544/337; 544/406
[58] Field of Search .................. 544/337; 424/200

[56] References Cited

U.S. PATENT DOCUMENTS 4,085,211  4/1978  Cragoe et al. .................. 424/250

*Primary Examiner*—Donald G. Daus
*Assistant Examiner*—Lisa Jones
*Attorney, Agent, or Firm*—Michael C. Sudol, Jr.; Harry E. Westlake, Jr.

[57] ABSTRACT

The case involves novel 3-amino-N-[(phosphonoamino)iminomethyl]-6-halopyrazinecarboxamides, derivatives thereof and processes for preparing same. 3-Amino-N-(phosphonoaminoiminomethyl)-6-halopyrazinecarboxamides of the instant case are eukalemic agents possessing diuretic and natriuretic properties.

9 Claims, No Drawings

3-AMINO-N-[(PHOSPHONOAMINO)IMINOMETHYL]-6-HALOPYRAZINECARBOXAMIDE COMPOUNDS, COMPOSITIONS AND METHODS OF USE

SUMMARY OF THE INVENTION

The instant case covers novel 3-amino-N-[(phosphonoamino)iminomethyl]-6-halopyrazinecarboxamides, derivatives thereof and processes for making the same. The novel compounds of this invention are depicted in Formula I below.

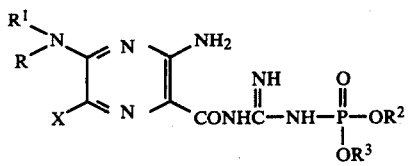

wherein
R is hydrogen,
  lower alkyl having from 1 to 5 carbon atoms such as methyl, ethyl, isopropyl, n-butyl or n-pentyl;
  lower alkenyl having from 2 to 5 carbon atoms such as allyl;
  lower alkynyl having from 2 to 5 carbon atoms such as propargyl;
$R^1$ is hydrogen,
  lower alkyl having from 1 to 5 carbon atoms such as methyl, ethyl, isopropyl, n-butyl or n-pentyl;
  lower alkenyl having from 2 to 5 carbon atoms such as allyl;
  lower alkynyl having from 2 to 5 carbon atoms such as propargyl;
$R^2$ is hydrogen,
  lower alkyl having from 1 to 5 carbon atoms such as methyl, ethyl, isopropyl, n-butyl or n-pentyl,
  benzyl and an alkali metal such as sodium, potassium or lithium;
$R^3$ is hydrogen,
  lower alkyl having from 1 to 5 carbon atoms such as methyl, ethyl, isopropyl, n-butyl or n-pentyl,
  benzyl and an alkali metal such as sodium, potassium or lithium; and X is halo, such as fluoro, chloro, bromo or iodo.

Preferred compounds are those compounds of Formula I wherein $R^2$ and $R^3$ are lower alkyl having from 1 to 5 carbon atoms or sodium, X=Cl and $R^1$ and $R^2$ are hydrogen.

The compounds of this invention as shown by Formula I and the preferred compounds discussed above are useful because they possess diuretic and natruiuretic properties. In addition, they are useful eukalemic saluretics, in other words, the compounds of the instant case cause neither loss or abnormal retention of potassium ions. Thus, the compounds of the instant invention are useful for the treatment of edema and hypertension and other decreases or conditions known to be responsive to this therapy.

The products of this invention can be administered to patients (both human and animal) in the form of pills, tablets, capsules, elixirs, injectable preparations and the like. They can be administered either orally or parentally or any other feasible method as known to those skilled in the art such as intravenously or in the form of suppositories and the like.

The type of formulation to be administered can be comprised of one or more of the compounds of this invention as the only essential active ingredient of the pharmaceutical formulation. The formulations are merely combinations of the active ingredient mentioned with pharmaceutically inert carriers and the like.

The compounds of this invention are advantageously administered at a dosage range of from about 5 mg. to about one gram per day or a somewhat higher or lower dosage at the physician's discretion, preferably in subdivided amounts on a 2 to 4 times a day regimen and most preferably at a dosage range from 10 to 500 mg. per day. It will be realized by those skilled in the art that the dosage range for any particular patient (animal or human) will depend upon the severity of the disease treated, weight of the patient and any other condition which the physician or other person skilled in the art will take account of.

The compounds disclosed in this invention in Formula I and the preferred compounds can be prepared according to the two processes described below.

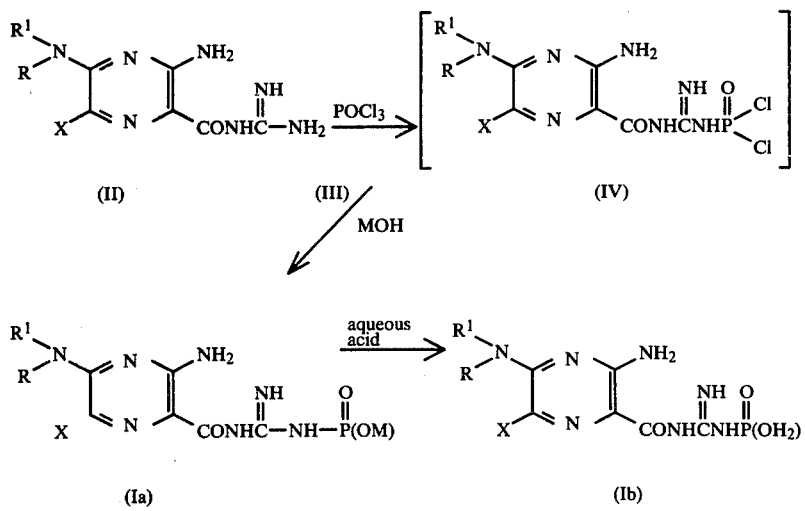

wherein R, $R^1$ and X are as previously defined and M is an alkali metal.

In this process, a pyrazinoylguanidine (II) is reacted with phosphorousoxychloride (III) to form an intermediate (IV) which is not isolated but reacted in situ with an alkali metal hydroxide to form the desired product (I). The reaction is usually run in an inert solvent such as pyridine, dimethylformamide or tetrahydrofuran generally at a temperature of from 0° C. to room temperature.

The reaction is also run in the presence of a hydrohalide acceptor such as triethylamine, pyridine or DBN (1,5-diazabicyclo[4.3.0]non-5-ene) or an excess of the guanidine component I may serve as the hydrohalide acceptor to take up the HX by-product of the reaction.

Although time is not critical the reaction is usually run at from 1 to 8 hours. Generally a 1 to 1 mole ratio of the reactants (II) and (III) are also used.

The intermediate product (IV) formed is not isolated but further reacted with an excess of alkali metal hydroxide (MOH) to give the desired alkali metal salt I. The MOH is added to the reaction mixture and stirred briefly at which time the alkali metal salt Ia usually precipitates and is isolated, for example by filtration.

The alkali metal salt product Ia can be converted to the free acid Ib by reaction of Ia with an aqueous mineral acid such as HCl or $H_2SO_4$. Generally an excess of the acid is added and the reaction mixture stirred at room temperature until the product Ib is formed. The free acids IB can be isolated by known means such as by filtration.

None of the reaction conditions described above are critical and they can be varied by those skilled in the art.

The second method for preparing compounds Ic of this invention can be depicted as follows:

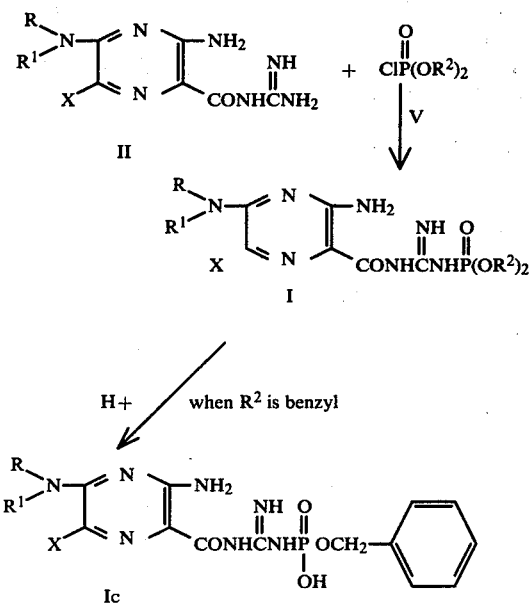

wherein R, $R^1$ and X are as previously defined and $R^2$ is lower alkyl or benzyl.

In this process a pyrazinoyl guanidine II is reacted with a disubstituted chlorophosphate V to form the desired product I. The reaction is run in an inert solvent such as pyridine, dimethylformamide or tetrahydrofuran at a temperature of 0° to room temperature.

The reaction is also run in the presence of a hydrohalide acceptor such as triethylamine, pyridine or DBN(1,5-diazabicyclo[4.3.0]non-5-ene) or an excess of the guanidine component I may serve as the hydrohalide acceptor to take up the HX by-product of the reaction.

Although time is not critical the reaction is usually run at from 1 to 8 hours. Generally a 1 to 1 mole ratio of the reactants (II) and (V) are also used.

If $R^2$ is benzyl then the product can be acidified with aqueous mineral acid such as HCl or $H_2SO_4$ preferably in an inert solvent such as acetone to obtain Ic.

None of the reaction conditions such as temperature or time is critical in the above described reactions and they can be varied by those skilled in the art.

All the guanidine starting materials (II) used in the process described above are shown in and disclosed in U.S. Pat. No. 3,313,813 mentioned previously or at least can be obviously prepared from compounds disclosed in the aforementioned patent.

The examples which follow illustrate the pyrazinecarboxamide products of the present invention and the methods by which they are prepared. However, the examples are illustrative only and it will be apparent to those having ordinary skill in the art that all the products embraced by the above-given description of the present invention may also be prepared in an analogous manner by substituting the appropriate starting materials for those set forth in the examples

EXAMPLE 1

Disodium N-[(3,5-diamino-6-chloropyrazinamido)imino-methyl]-phosphoramidate monohydrate A stirred suspension of N-amidino-3,5-di-amino-6-chloropyrazinecarboxamide (9.2 g., 0.04 mole) in pyridine (150 ml.) is cooled to 10° C. and treated dropwise with phosphorous oxychloride (1.8 ml., 0.02 mole) during a ½ hour period. After 3 hours N-amidino-3,5-diamino-6-chloropyrazinecarboxamide hydrochloride is filtered and the pyridine filtrate treated with 5 N sodium hydroxide (10 ml.) to give disodium N-[(3,5-diamino-6-chloropyrazinamido)iminomethyl]-phosphoramidate monohydrate which melts at >300° C. after recrystallization from ethanol-water.

Elemental analysis for $C_6H_7ClN_7O_4PNa_2.H_2O$
Calc.: C, 19.39; H, 2.44; Cl, 9.54; P, 8.34; Found: C, 19.00; H, 2.14; Cl, 9.47; P, 7.99.

EXAMPLE 2

Diethyl N-[(3-amino-6-chloro-5-isopropylaminopyrazinamido)iminomethyl]phosphoramidate A stirred solution of N-amidino-3-amino-5-isopropylamino-6-chloropyrazinecarboxamide (2.7 g., 0.01 mole) and DBN (1.24 g., 0.01 mole) in tetrahydrofuran (100 ml.) is cooled to 10° C., treated with diethyl chlorophosphite (1.44 ml., 0.01 mole), then stirred at 25° for one hour. The reaction mixture is filtered evaporated to a volume of 5 ml. and treated with water (100 ml.) to give diethyl N-[(3-amino-6-chloro-5-isopropylaminopyrazinamido)iminomethyl]phosphoramidate which melts at 166° C. after recrystallization from isopropanol-water.

Elemental analysis for $C_{13}H_{23}ClN_7O_4P$;
Calc.: C, 38.29; H, 5.68; N, 24.04; Found: C, 38.31; H, 5.68; N, 24.41.

EXAMPLE 3

Diethyl N-[(3,5-diamino-6-chloropyrazinamido)iminomethyl]-phosphoramidate

A stirred solution of N-amidino-3,5-diamino-6-chloropyrazinamide (4.6 g., 0.02 mole) and DBN (2.5 g., 0.02 mole) in dimethylformamide (300 ml.) is cooled to 10° C. and treated with diethyl chlorophosphite (2.9 ml., 0.02 mole). The reaction is stirred at 25° C. for 3 hours, filtered and treated with ice water (300 ml.) to give diethyl N-[(3,5-diamino-6-chloropyrazinamido)iminomethyl]phosphoramidate which melts at 230° C. after recrystallization from ethanol-water.

Elemental analysis for $C_{10}H_{17}ClN_7O_4P$;
Calc.: C, 32.84; H, 4.69; N, 26.81; Found: C, 32.80; H, 4.73; N, 26.77.

EXAMPLE 4

Dibenzyl N-[(3,5-diamino-6-chloropyrazinamido)iminomethyl]-phosphoramidate

A stirred solution of N-amidino-3,5-diamino-6-chloropyrazinamide (4.6 g., 0.02 mole) and DBN (2.5 g., 0.02 mole) in dimethylformamide (150 ml) is treated with dibenzylchlorophosphite (6.6 g., 0.22 mole) in one portion. The reaction mixture is stirred at 25° C. for 18 hours, filtered and treated with water to precipitate dibenzyl N-[3,5-diamino-6-chloropyrazinamido)iminomethyl]phosphoramidate which melts at 187° C.

Elemental analysis for $C_{20}H_{21}ClN_7O_4P$;
Calc.: C, 49.03; H, 4.32; N, 20.02; Found: C, 48.64; H, 4.14; N, 19.89.

EXAMPLE 5

Benzyl N-[(3,5-diamino-6-chloropyrazinamido)iminomethyl]-phosphoramidate

A stirred suspension of dibenzyl N-[(3,5-diamino-6-chloropyrazinamido)iminomethyl]phosphoramidate (0.98 g., 0.002 mole) in acetone (100 ml.) is treated with 1 N hydrochloric acid (4.1 ml., 0.0041 mole) which causes the reaction mixture to become homogeneous. The reaction mixture is filtered and refrigerated overnight during which time benzyl N-[(3,5-diamino-6-chloropyrazinamido)iminomethyl]-phosphoramidate precipitates. M.p. 244° C.

Elemental analysis for $C_{13}H_{15}ClN_7O_4$;
Calc.: C, 39.06; H, 3.78; N, 24.54; Found: C, 38.89; H, 3.91; N, 24.24.

What is claimed is:

1. A compound of the formula

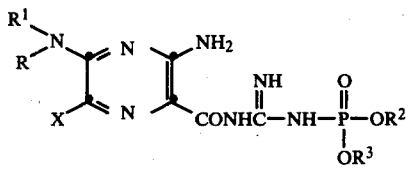

wherein

R is hydrogen, lower alkyl, lower alkenyl or lower alkynyl;

$R^1$ is hydrogen, lower alkyl, lower alkenyl or lower alkynyl;

$R^2$ is hydrogen, lower alkyl, benzyl or alkali metal;

$R^3$ is hydrogen, lower alkyl, benzyl or alkali metal; and

X is halogen.

2. A compound of the formula

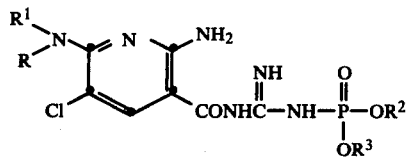

wherein

R and $R^1$ are hydrogen;

$R^2$ and $R^3$ are lower alkyl having up to 5 carbon atoms or sodium.

3. A compound of claim 2 which is disodium N-[(3,5-diamino-6-chloropyrazinamido)iminomethyl]phosphoramidate monohydrate.

4. A compound of claim 2 which is diethyl N-[3,5-diamino-6-chloropyrazinamido)iminomethyl]phosphoramidate.

5. A compound of claim 1 which is diethyl N-[(3-amino-6-chloro-5-isopropylaminopyrazinamido)iminomethyl]phosphoramidate.

6. A compound of claim 1 which is dibenzyl N-[(3,5-diamino-6-chloropyrazinamido)iminomethyl]phosphoramidate.

7. A compound of claim 1 which is benzyl N-[(3,5-diamino-6-chloropyrazinamido)iminomethyl]phosphoramidate.

8. A method of treating edema and/or hypertension which comprises administering to a patient a pharmacologically acceptable dose of a compound of the formula:

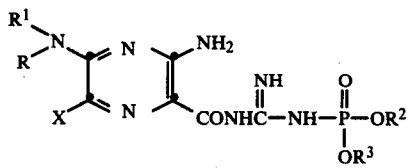

wherein

R is hydrogen, lower alkyl, lower alkenyl or lower alkynyl;

$R^1$ is hydrogen, lower alkyl, lower alkenyl or lower alkynyl;

$R^2$ is hydrogen, lower alkyl, benzyl or alkali metal;

$R^3$ is hydrogen, lower alkyl, benzyl or alkali metal; and

X is halogen.

9. A pharmaceutical composition useful in the treatment of edema and hypertension consisting essentially of, as an active ingredient, a compound of the formula:

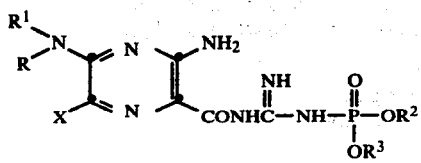
wherein
R is hydrogen, lower alkyl, lower alkenyl or lower alkynyl;
$R^1$ is hydrogen, lower alkyl, lower alkenyl or lower alkynyl;
$R^2$ is hydrogen, lower alkyl, benzyl or alkali metal;
$R^3$ is hydrogen, lower alkyl, benzyl or alkali metal;
X is halogen, and
a pharmaceutically acceptable inert carrier.
* * * * *